United States Patent [19]

Hayman et al.

[11] Patent Number: 5,267,960
[45] Date of Patent: Dec. 7, 1993

[54] TISSUE ENGAGING CATHETER FOR A RADIOACTIVE SOURCE WIRE

[75] Inventors: Michael Hayman, New Orleans; Sam F. Liprie, Lake Charles, both of La.

[73] Assignee: Omnitron International Inc., Houston, Tex.

[21] Appl. No.: 829,606

[22] Filed: Jan. 29, 1992

Related U.S. Application Data

[63] Continuation of Ser. No. 495,093, Mar. 19, 1990.

[51] Int. Cl.[5] ............................................ A61M 27/00
[52] U.S. Cl. ...................................... 604/106; 604/174
[58] Field of Search ........ 604/174, 175, 180, 104–106; 606/198

[56] References Cited

U.S. PATENT DOCUMENTS

| | | | |
|---|---|---|---|
| 2,569,008 | 9/1951 | Kraft | 15/104.31 |
| 3,490,456 | 1/1970 | Kortum | 604/106 |
| 3,592,197 | 7/1971 | Cohen | 604/280 |
| 4,043,346 | 8/1977 | Mobley et al. | 606/198 |
| 4,643,184 | 2/1987 | Mobin-Uddin | 606/198 |
| 4,654,028 | 3/1987 | Suma | 606/198 |
| 4,909,789 | 3/1990 | Taguchi et al. | 606/198 |
| 4,994,069 | 2/1991 | Ritchart et al. | 606/198 |

Primary Examiner—C. Fred Rosenbaum
Assistant Examiner—Manuel Mendez

[57] ABSTRACT

A device for installing a catheter in a patient's body for use in delivery of a radioactive source to and from the site of a tumor so that it may be shrunk. The device includes a catheter and apparatus for implanting the catheter through the tumor site so that the distal end of the catheter extends beyond the site, with the proximal end exposed externally of the body to permit entry and withdrawal of the radioactive source. A selectively deployable anchor at the distal end of the catheter is adapted to penetrate body tissue at the distal end beyond the tumor site when the anchor is deployed. Consequently, the distal end of the catheter will be securely anchored to maintain a substantially constant lineal depth from the proximal end of the catheter to the tumor site. The radioactive source can then be driven through the catheter to the tumor site to irradiate the tumor for a prescribed period, and then withdrawn. The patient remains ambulatory with the catheter in place between fractionated periodic treatments, and yet repetitive radiation treatment consistently at the precise desired location is assured.

15 Claims, 5 Drawing Sheets

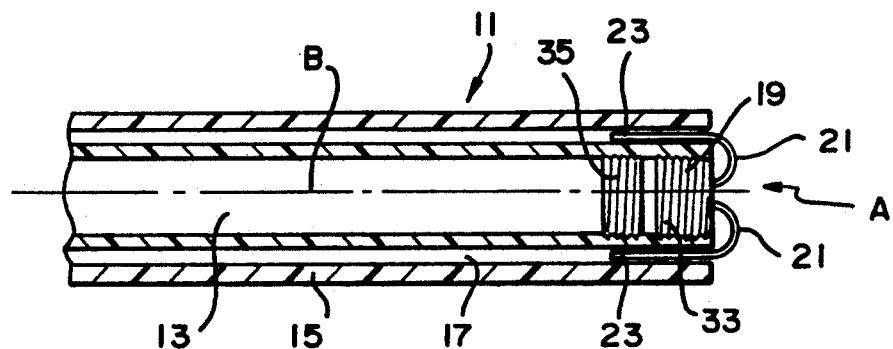
FIG. IA
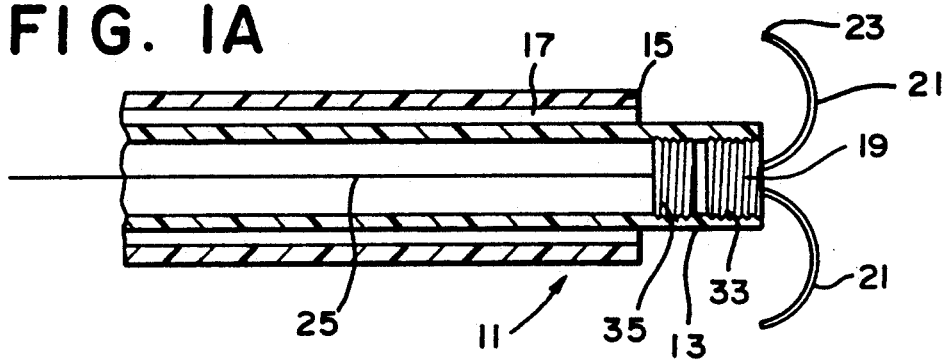
FIG. IB
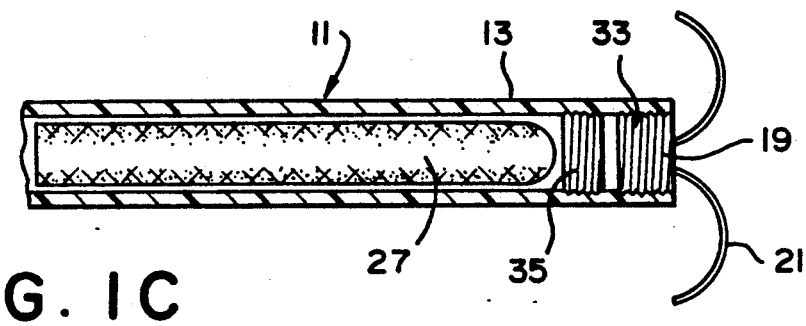
FIG. IC
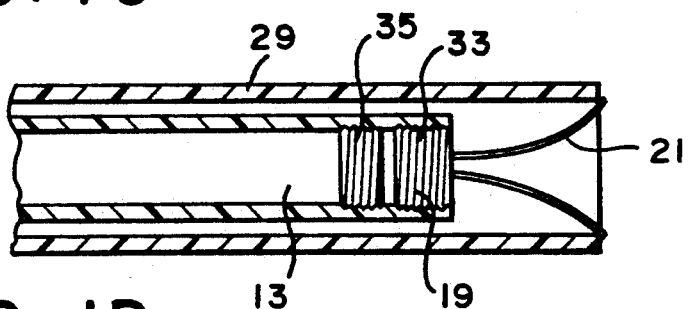
FIG. ID
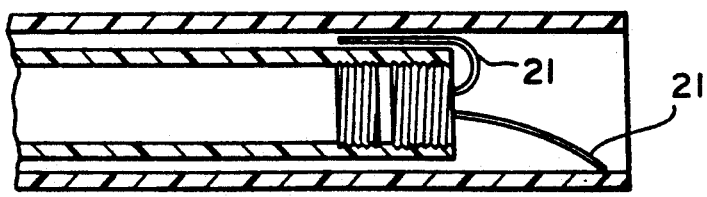
FIG. IE

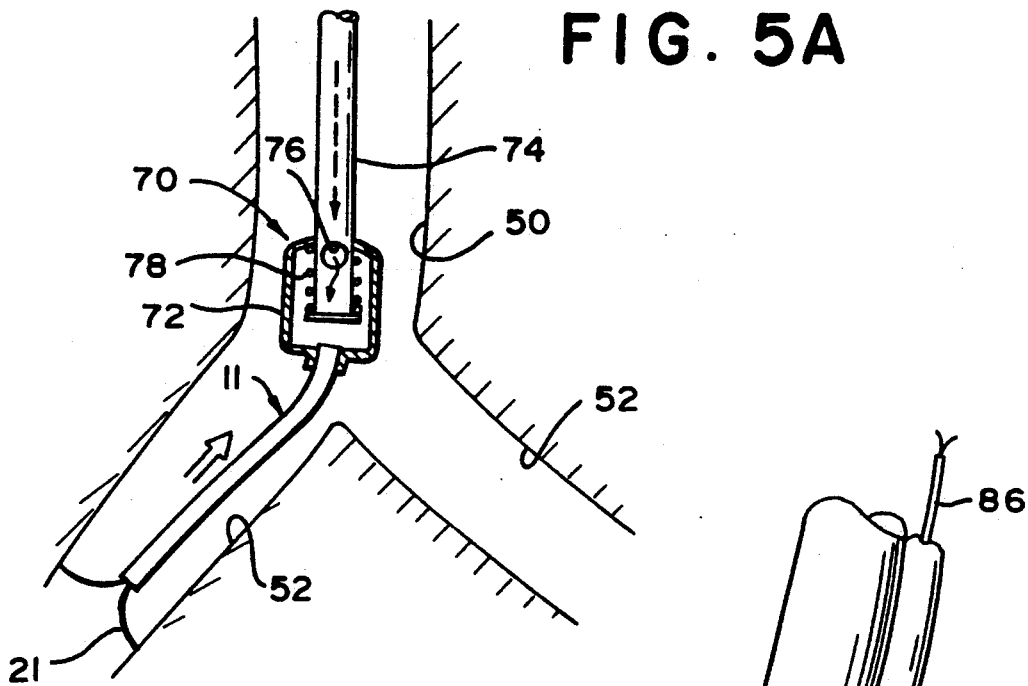
FIG. 5A
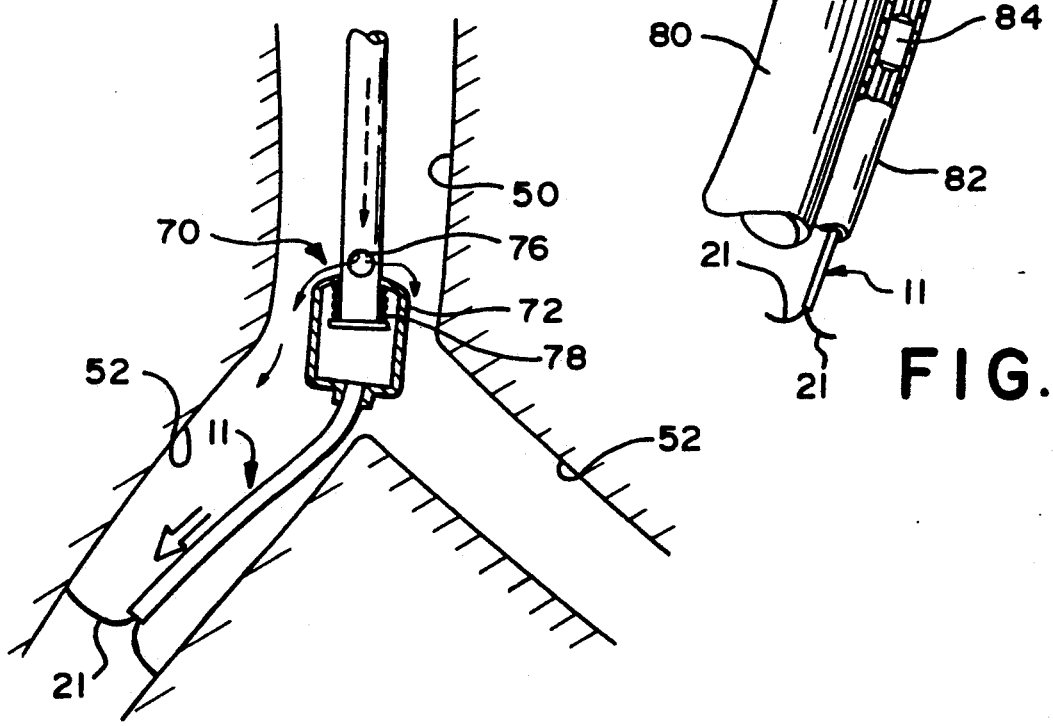
FIG. 5B
FIG. 6

TISSUE ENGAGING CATHETER FOR A RADIOACTIVE SOURCE WIRE

This application is a continuation of application Ser. No. 07/495,093, filed Mar. 19, 1990.

BACKGROUND AND SUMMARY

The present invention generally relates to a catheter for insertion into a body for treatment thereof, and more particularly, to a catheter having a unique anchoring arrangement for releaseably anchoring the catheter at a desired treatment site in the body without the need for the catheter to be positioned in a vessel, body cavity or the like in order to facilitate the attachment of the catheter as well as to methods of utilizing the catheter.

One catheter having an anchoring arrangement for retention within the body is the Foley catheter. Commonly referred to as a balloon catheter, the Foley catheter has a balloon at its inner end which is inflated to wedge the catheter within an opening of the body, for example, the bladder. Disadvantages of the balloon catheter arrangement include the fact that the catheter must be positioned within a vessel or body cavity to provide a space in which the inflated balloon is held in order to facilitate attachment of the catheter. Further, the inflatable balloon, once inflated, does not always reliably deflate as required which can cause difficulties during removal as well as possible injury to the patient.

Alternative arrangements for anchoring medical devices within the body include the use of flexible feelers as disclosed by U.S. Pat. No. 3,467,090. These flexible feelers extent from a base into an end of a tube and project outwardly through openings in a sleeve at a substantial distance to positively engage with the cervical canal only when in the operating position.

A further catheter, also designed for positioning in a body cavity, such as, the bladder, is disclosed by U.S. Pat. No. 4,043,346 wherein an inner tubular member having a rounded expansion tip at its inner end is slidably mounted inside an outer tubular member. The rounded expansion tip of this catheter comprises a plurality of prongs biased outwardly and operable to expand and open when the prongs are pushed beyond an inner end of the outer tubular member. The prongs retract upon movement of the inner tubular member to a position where at least a portion of the prongs are within the outer tubular member.

While the above-noted anchoring arrangements are operationally quite efficient, none of these devices are adapted for precise positioning of a catheter at a desired location in the body without the requirement that the catheter be positioned within a body cavity in order to anchor the catheter. Since they engage and nest against the inner surface of the cavity, they do not stay firmly in place, especially for irregular surfaces. Moreover, the noted devices make no provision for using a catheter in the treatment of cancerous tumors wherein the catheter is inserted within the human body and left in place for several days to provide a sterile channel by which daily fractionation treatments to cancerous areas which can be conducted for up to several days at a time.

Oxygen therapy supplies oxygen through tubes from an external source to the pulmonary system. The tubes have included a nasal cannula and transtracheal tubes. To conserve oxygen, the exhalation portion of the cycle is sensed. The "Oxymizer" pendant senses the change in pressure mechanically to determine the exhalation portion. The "Oxymatic" is an electronic demand pulsed-oxygen delivery device. Generally pressure transducers have been used to determine the expiratory of the cycle. Depending upon the placement of the pressure transducer, the pressure may be altered by mouth breathing and other variables, thus there is a need for a sensing device which is not dependent on pressure to determine the expiratory portion of the cycle. These devices make no provision for using a catheter as a sensor for controlling the flow of transtracheal oxygen to the lungs so that oxygen is only delivered during the inspiratory phase of the respiratory cycle.

Accordingly, it is an object to the present invention to provide a catheter having a simple anchoring arrangement which permits attachment of a distal end of the catheter at a desired treatment site without the requirement to position the catheter within a body cavity to facilitate attachment.

A further object of the present invention is to provide a catheter having a simple anchoring arrangement which permits reliable removal of the catheter after completion of treatment.

It is yet another object of the present invention to provide a catheter and anchoring arrangement with a very small outside diameter so that the catheter can be introduced into the body within a needle and attached at areas inside the body which are accessible, without surgery, only by a needle.

It is also an object to the present invention to provide a catheter which forms a closed channel extending from a location outside of the body to a treatment site inside the body which prevents the introduction of foreign matter into the body that cause infection while still providing treatment access to the treatment site by means of a dedicated, sterile channel.

It is a further object of the present invention to provide a catheter which is adapted to be left in place at the desired location for several days to permit extended and/or multiple treatments of the treatment site, and can be reliably removed from the body on an outpatient basis without the need for surgery.

Still a further object of the present invention is to provide different methods of using the catheter to treat, for example, tumors, such as, deep dwelling tumors and the like, wherein the closed sterile channel, formed by the catheter, is employed to deliver treatment materials, such as, radioactive materials, to the distal end of the catheter positioned at the treatment site.

It is a further object of the present invention to provide a method of using the catheter to sense the inspiratory phase of a respiratory cycle to control the delivery of transtracheal oxygen to the lungs only during the inspiratory phase as well as a specialized configuration of the catheter for use as a sensor to control the flow of transtracheal oxygen to the lungs.

The unique catheter, according to advantageous embodiments of the present invention, permits treatment access to a wide variety of areas inside the body on an out-patient basis without the need for surgery. The catheter is typically provided with an overall diameter which permits insertion of the catheter into the body inside an opening of a flexible or rigid scope, for example, an endoscope or bronchoscope, to treat areas of the body which are accessible by such devices.

Further, due to its small diameter and at least the end being constructed of fluoroscopically opaque materials, that catheter can be placed into the body through a needle, so that, under a fluoroscope, the catheter is positioned anywhere in the body accessible by a needle to treat tumors or the like without the use of surgery.

Additionally, because the catheter is a closed system catheter, no foreign matter can enter the body through the catheter and cause infection which can occur during surgery.

Moreover, the catheter is provided with an unique anchoring arrangement which is simple, permits precise attachment of the distal end of the catheter at a treatment site without the need to position the catheter within a body cavity, and has a simple removal technique for reliably detaching the anchor for removal of the catheter.

Further, the catheter can be provided with a fail-safe removal arrangement which permits detachment of the anchor from the catheter to permit removal.

These and other objects and advantages are achieved according to preferred embodiment of the present invention by a catheter having an outer tubular member in which an inner tubular member is slidably disposed and spaced therefrom to form a storage space between the two members. An anchor for attaching the catheter at a treatment site is provided at a distal end of the catheter and is stored in the storage space between the inner and outer members.

The anchor comprises at least one, spring-loaded, hook-shaped arm which forms a barb when released from the storage space for penetrating surrounding tissue. The arm is attached at one end to the distal end of the inner tubular member and has a tissue penetrating end which is bent-back away from the distal end of the inner tubular member when the arm is deployed so as to firmly lodge into surrounding tissue. The arm is held in a stored, spring-loaded position at the storage space between the inner and outer members during insertion of the catheter into the body so as to be positioned substantially parallel to a longitudinal axis of the inner tubular member.

Relative slidable movement between the inner and outer member frees the tissue penetrating end of the spring-loaded arm from the storage space to permit the arm to swing out and away from the distal end of the inner tubular member and catch on tissue at the treatment site to anchor the catheter as desired. As the inner tubular member is pulled back, the bent-back tissue penetrating end of the anchor arm is driven into the surrounding tissue, much like a fish hook, to anchor the distal end of the catheter at a desired treatment site. The outer tubular member can then be completely removed from the inner tubular member and the body.

With a proximal end of the inner tubular member extending out of the body and the distal end closed, a closed channel is formed which terminates at the distal end of the inner tubular member positioned at the treatment site. The closed channel thus provides a sterile route by which treatment materials, for example radioactive materials, can be guided, in a dedicated manner, precisely and accurately to the treatment site.

To provide a simple catheter removal technique, a larger, outer sleeve or removal tube is inserted back over the inner tubular member and is pushed along the inner tubular member until this outer sleeve reaches the anchor. At this point, the inner tubular member is held stationary as the outer sleeve is advanced. This movement causes the arm of the anchor to bend in a backwards motion forcing the arm to withdrawn from and release its hold on the surrounding tissue. The spring-loaded arm of the anchor is then pulled back through the inside diameter of the outer sleeve so that it can no longer catch on the surrounding tissues and the entire catheter assembly is removed from the body.

According to another embodiment of the present invention, a second arrangement for detaching the anchor to permit removal of the catheter is provided wherein the anchor is releaseably connected to the distal end of the inner tubular member by a threaded arrangement. With a simple twisting of the inner tubular member, the threaded connection releases the anchor therefrom to permit removal of the catheter from the body. To maintain a closed system, the distal end of the inner tubular member is sealed upstream of the anchor. This arrangement is particularly useful when it is not possible to insert the outer sleeve back over the inner tubular member to remove the anchor from the body as discussed above. Further, since the anchor is preferably made of a stainless steel material, it does not interfere with body functions or cause any problems to the body when the anchor is left within the body.

According to yet a further embodiment of the present invention, the anchor comprises two bent-back, spring-loaded, stainless steel wire arms which each form a barb.

Methods of using the catheter to provide treatment inside the body include, but are not limited to, treatment of lung tissue, cervical tissue, pelvic tissue, interstitial, percutaneous type lesions, deep indwelling tumors, and the like.

A further and advantageous method of using a catheter which can be secured to an internal cavity without surgery includes the sensing of an inspiratory phase of the respiratory cycle to control the delivery of oxygen to the lungs only during the inspiratory phase. This arrangement is particularly advantageous in the controlled delivery of transtracheal oxygen which is administered to treat chronic respiratory insufficiency. Here, the distal end of the catheter is attached in a small peripheral bronchiole of the lung where it moves about 1 to 2 cm with each movement of the diaphragm during inhalation. By employing the movement of the distal end to trigger an electronic or mechanical switch which controls the operation of a flow valve, oxygen is delivered to the tracheal junction of the lungs only during the inspiration phase of the respiratory cycle. Although the securing device of the present invention is preferred, any device which will secure the catheter to the bronchiole can be used.

This control arrangement greatly reduces the loss of oxygen delivered to the lungs during the expiratory phase of the breathing cycle which is pushed out with expired carbon dioxide and wasted. Moreover, the transtracheal oxygen delivered by this method maintains the same blood level of oxygen with a much lower flow rate thereby reducing the amount of oxygen used as well as the cost of treatment.

These and other objects, advantages and novel features of the present invention will become apparent from the following detailed description of the invention when considered in conjunction with the accompanying drawings.

BRIEF DESCRIPTION OF THE DRAWINGS

FIGS. 1A-1E are cross-sectional views illustrating insertion, release, treatment, and removal configurations for a catheter according to one embodiment of the present invention;

FIGS. 5A, 5B and 6 illustrate a further embodiment of the present invention wherein the catheter is employed as a switch to control the delivery of transtracheal oxygen only during the inspiration phase of the respiratory cycle; and

DETAILED DESCRIPTION OF THE DRAWINGS

Referring to FIGS. 1A-1E, a catheter, generally indicated at 11, is illustrated which comprises an inner tubular member 13 slidably disposed within an outer tubular member 15 so as to form a storage space 17 therebetween.

The inner tubular member 13 is preferably made of teflon, silicone, tygon or similar substance to reduce friction during the relative slidable movement between these members 13, 15, the outer tubular member 15 being preferably made of a polyester, teflon, silicone, stainless steel or similar material.

Figure 3A:
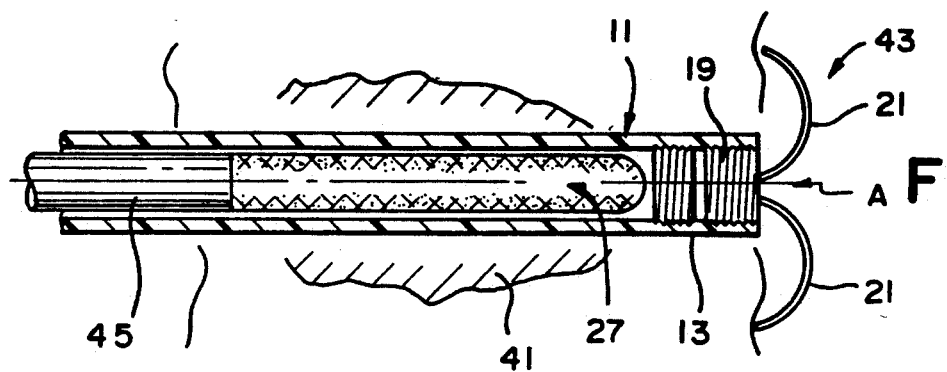
FIGS. 3A-3C are cross-sectional views illustrating alternative removal techniques for different embodiments of the catheter of the present invention.

A distal end of the inner tubular member 13, generally indicated at A, is closed, for example, by a permanent plug 35 and provided with an anchor 19 for precisely attaching the distal end A of the catheter 11 at a desired treatment site within a body. One end of each of the arms 21 is attached to the distal end A of the inner tubular member 13 by, for example, a detachable screw plug 33. Alternatively, the one end of each of the arms is connected directly to a closed distal end A of the catheter 11. The permanent plug 35 seals the distal end of the inner tubular member 13 upstream of the detachable screw plug 33. The anchor 19 comprises one or more spring-loaded, hook-shaped arms 21 which each form a barb for lodging firmly into surrounding tissue to prevent the inner tubular member 13 from advancing further into or out of the body once the barb is securely locked in place in the tissue as shown in FIGS. 1C and 3A.

An open proximal end of the inner tubular member 13 (not shown) then protrudes out of the body to form a closed channel into the body through which treatment materials, such as, for example, radioactive materials 27 as seen in FIG. 1C, are implanted and conveyed to a treatment site, at which the distal end A of the catheter 11 is located, on a daily basis if required to permit multiple treatments of the treatment site.

The other end of the each of the arms 21 forms a tissue penetrating end 23 which is bent-back away from the distal end A of the inner tubular member 13 to form a barb which penetrates about 1 mm into the tissue when the anchor 19 is deployed as shown in FIG. 1C. During insertion of the catheter 11, the anchor 19 is stored in the storage space 17, as shown in FIG. 1A, with each of the arms 21 bent back approximately 180° so as to be positioned substantially paralleled to a longitudinal axis B of the inner tubular member 13. Alternatively, one or more of the arms 21 may extend forward and in combination with a rearward extending arm will assure securement in both axial directions as illustrated in FIG. 1E.

Relative slidable movement between the inner and outer tubular members 13, 15, as illustrated in FIG. 1B, frees the tissue penetrating ends 23 of the pair of spring-loaded, hook-shaped arms 21 from the storage. This permits the arms 21 of the anchor 19 to swing out and way from the distal end A of the inner tubular member 15 and penetrate tissue at a treatment site to anchor the catheter 11 as shown in FIG. 1C and as will be further described hereinafter with reference to FIG. 3A.

In order to facilitate the relative slidable movement between the inner and outer tubular members 13, 15, a small, removable back-bone wire 25 is provided inside the inner tubular member 13. Pushing the small, removable back-bone wire 25 forward, once the catheter 11 is introduced into the body, causes the inner tubular member 13 to advance forward relative to the outer tubular member to enable the spring-loaded arms 21 of the anchor 19 to be released from the storage space 17 and open up. Alternatively, the outer tubular member 15 can be pulled back to release the arms 21 or a combination of the two types of relative movement can be employed to release the arms 21 from the storage space causing them to open up and swing away from the distal end of the catheter 11 as seen in FIG. 1C. The inner member 13 is then pulled back to drive the extended arms 21 into the surrounding tissue to thereby anchor the catheter 11 as desired.

According to one preferred embodiment of the present invention, each of the two spring-loaded, hook-shaped arms 21 comprise a hook-shaped wire member preferably made of a biologically inert material, such as, for example, stainless steel. The wire arms 21 are formed to assume the desired hook-shape upon release from the storage position within the storage space 17 so that when the arms 21 are deployed, a tangent at the tissue penetrating end 23 of the wire arms 21-forms an angle of less than about 90° with the longitudinal axis B of the inner tubular member 13. This configuration of the wire arms 21 permits easy insertion and Penetration of the anchor 19 into tissue at a treatment site as the inner tubular member 13 is pulled back once the arms 21 have been released from the storage space 17.

Although two arms 21 are shown in the drawing figures of the present application for the anchor 19, it is understood that a single arm or any greater number of arms can be provided in accordance with the catheter of the present invention.

Referring to FIG. 1D, one method of detaching the anchor 19 from the surrounding tissues is illustrated wherein an outer sleeve or removal tube 29 is pushed along the inner tubular member 13 to the distal end A at which the anchor 19 is positioned. The advancement of the outer sleeve 29, as the inner tubular member 13 is held stationary, causes the arms 21 to bend in a backwards motion forcing the arms to become dislodged from the tissue. As the outer sleeve 29 is pushed further forward, the arms 21 are completely dislodged from the tissue and then withdrawn into the sleeve 29 by pulling back on the inner tubular member 13 as the removal tube 29 is held stationary. Thereafter, the entire assembly is removed from the body.

Alternatively, the inner member 13 can be rotated about its longitudinal axis B to unthread the threaded plug 33 to detach the anchor 19 from the distal end A of the inner member 13 and then the catheter 11 is withdrawn from the body. The different removal methods will be more fully described below with reference to FIGS. 3A-3C.

Figure 2A:
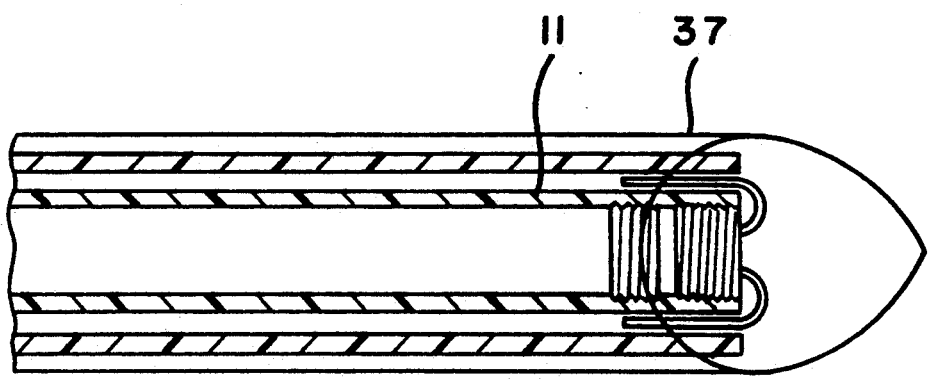
FIGS. 2A and 2B are cross-sectional views illustrating alternative arrangements for inserting the catheter of the present invention into a body.
Figure 2B:
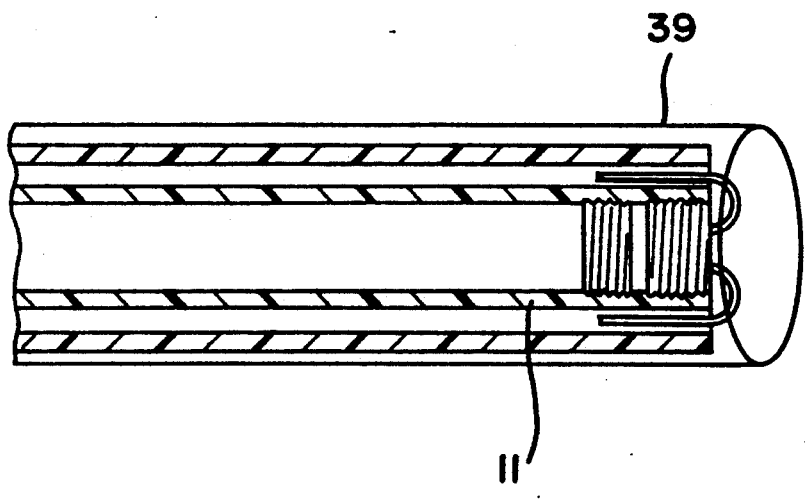

FIGS. 2A and 2B illustrate the catheter 11 configured for insertion into the body. As seen in FIG. 2A, with the anchor 19 stored in the storage space 17, the catheter 11 is inserted into the body through a needle 37, for example, having a gauge of 13 or larger. Alternatively, as illustrated by FIG. 2B, the catheter 11 can be inserted into the body by a flexible or rigid scope 39, such as, for example, a bronchoscope or an endoscope. Such scopes 39 oftentimes have devices which permit viewing of the interior of the body to permit positioning of the catheter 11. However, because at least the end of the the catheter 11 is constructed from fluoroscopically opaque materials, the physician can locate the catheter at any desired treatment location using a fluoroscope regardless of the method of insertion employed. The fluoroscopically opaque portion may be the plugs 33 and 35.

During the attachment procedure, as best seen in FIG. 3A, the distal end A of the catheter 11 is preferably inserted beyond a treatment site 41, for example, a tumor. The position of the distal end of the catheter is determined using a fluoroscope. Once the catheter 11 is properly positioned, the needle 37 or scope 39 is then removed from the body leaving the catheter 11 in place in the body. Thereafter, the inner tubular member 13 and outer tubular member 15 are slidably moved relative to one another, for example, by pulling the outer tubular member 15 back while leaving the inner tubular member 13 stationary using the removable back-bone wire 25 to hold the inner member 13. As a result, the arms 21 of the anchor 19 are freed from the storage space 17 and released so as to open up. As the inner member 13 is pulled back, the arms 21 embed in the surrounding tissue, generally indicated at 43 in FIG. 3A.

Once properly anchored, an iridium wire implant 27 is placed through the inner tube 13 by means of a stainless steel wire 45 to irradiate and treat the tumor at the treatment site 41, for example, a lung tissue. Cervical tissue tumor, cervic tissue tumor, pelvic tissue tumor, interstitial and percutaneous type lesions, deep indwelling tumors, and the like. The closed catheter may also receive other radioisotopes in wire or seed form as well as hyperthermia and photodynamic applicators.

As noted above, the catheter 11 can remain inside the body for several days during which extended fractionation treatments to cancerous areas can be performed for up to several days at a time. Further, due to the small diameter of the catheter 11, i.e., on the order of 3 mm, multiple catheters can be placed at a tumor bed without causing much trauma to a patient. A 20 gauge needle could be used for low dose iridum wire available in 0.3 mm diameters. A 12 gauge needle would be a practical large size limit; with the preferable range being between 14 gauge and 17 gauge.

Figure 3B:
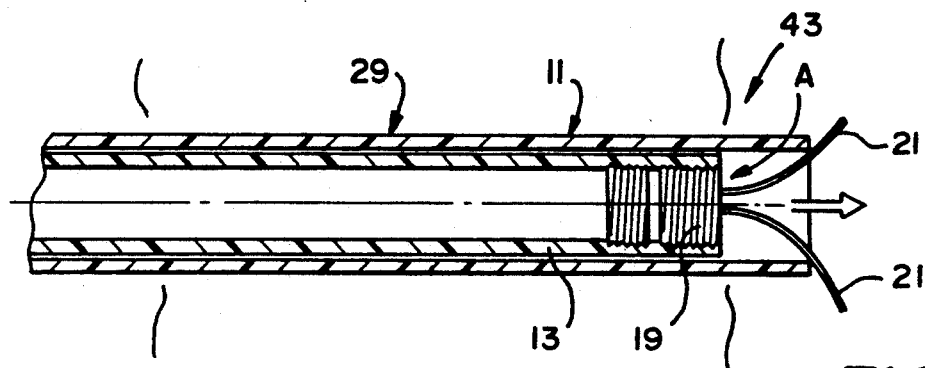

Once treatment is completed, the catheter 11 is removed from the body by one of two removal arrangements. As best seen in FIG. 3B, one removal arrangement utilizes the outer sleeve 29 which is slide over the inner tubular member 13 all the way to the distal end A at which the anchor 19 is positioned. This outer sleeve 29 preferably has a wall thickness in the range of about 0.1 mm to 2 mm depending upon the rigidity of the sleeve. The outer sleeve 29 is then pushed forward while holding the inner tubular member 13 stationary which causes the outer sleeve 29 to push on the arms 23 of the anchor 19 and release these arms 21 out of the body tissue 43 as described above. The pulling back of the inner tubular member 13 as the removal tube 29 is held stationary causes the arms 21 to retract back into the outer sleeve 29. Thereafter, the entire assembly, including the inner tubular member 13 with the attached anchor 19 and the outer sleeve 29, is removed from the body.

Figure 3C:
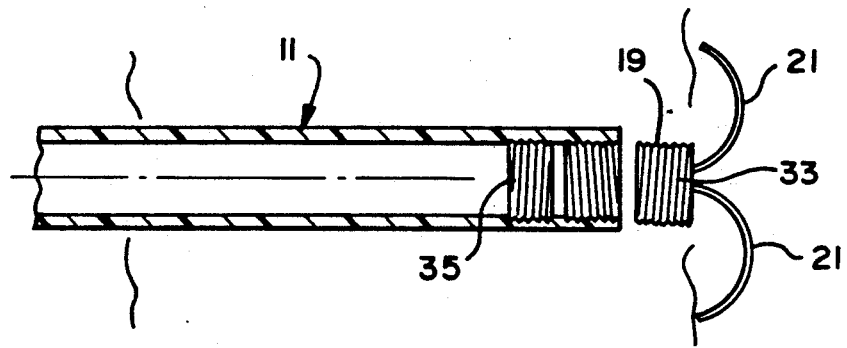

According to yet another embodiment of the present invention, the distal end A of the inner tubular member 13 is provided with a threaded connection, generally seen at 31 in FIGS. 1A-1D, which releaseably connects the anchor 19 at the distal end A of the inner tubular member 13. This comprises a detachable screw plug 33 which carries the anchor 19 and a permanent screw plug 35 permanently fitted at the distal end A of the inner tubular member 13. If it is not possible to insert the thick-walled outer sleeve 29 back-over the inner tubular member 13, the inner tubular member 13 can be turned counter clockwise about its longitudinal axis B thereby disengaging the screw plug 33 holding the anchor 19 from the distal A of the inner tubular member 13 as illustrated in FIG. 3C. Thereafter, the catheter 11 is be removed leaving the anchor 19 in the body. Because the anchor 19 is preferable made from surgical grade stainless steel, and is of an extremely small size, it will not interfere with body functions or cause any problems to the body.

Figure 4A:
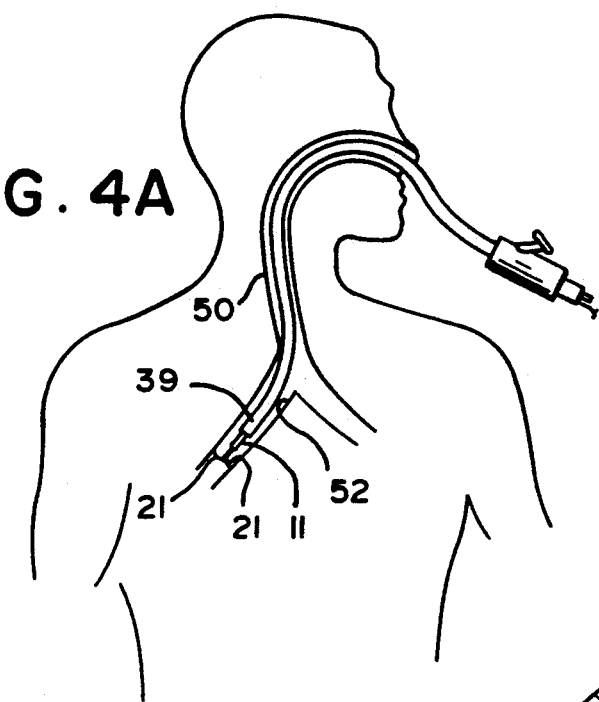
FIGS. 4A-4D illustrate the method of securement of the catheter in the bronchial tract.
Figure 4B:
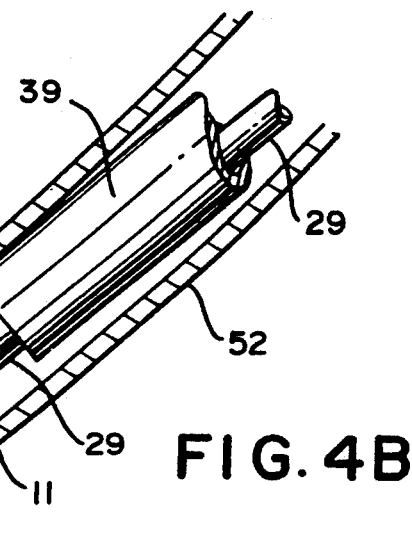

The treatment of a site within the lung or one of the bronchi will be described with respect to FIGS. 4A-4D. A catheter 11 with sleeve 29 are inserted by a bronchioscope 39 through the nasal passage down through the trachea bronchial 50 to one of the bronchi 52. Using a fiber optic bronchioscope guidance as well as a fluoroscope, the catheter 11 is lodged in the peripheral bronchial tree. The distal and proximal ends of the tumor tissue are then identified and the appropriate areas for treatment are marked by the bronchioscope in combination with the fluoroscope examination. The outer sleeve 29 is moved approximately one centimeter and the arms 21 embed themselves in the mucosa of the bronchial wall as illustrated in FIG. 4B. Radioactive wire may then be inserted through the catheter 11 for treatment at the tumor site.

Figure 4C:
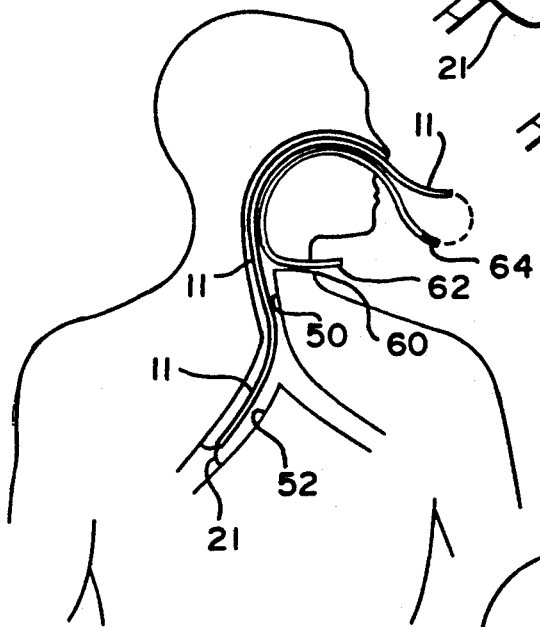
Figure 4D:
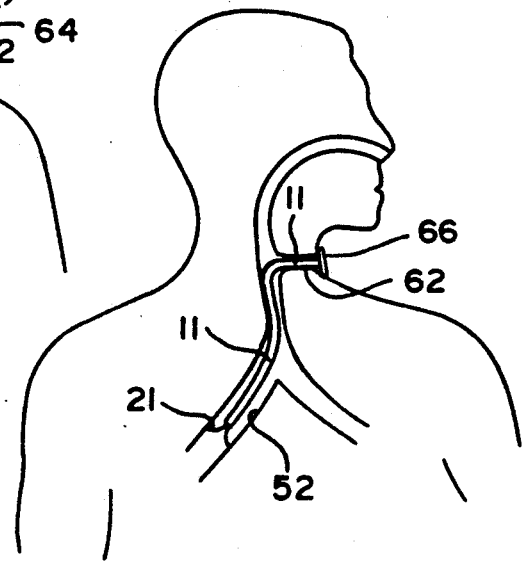

For a transtracheal implementation, a transtracheal cricothyroid opening 60 is made. A piece of tubing 62 with a stainless steel screw 64 is inserted through the transtracheal opening 60 up through the larynx, through the nasalpharnyx and out through the external nostril as shown in FIG. 4C. The fiber optic bronchioscope 39 is then withdrawn. The proximal end of the catheter 11 is then attached to the tubing 62 by the screw 64. The tubing 62 is withdrawn and the catheter 11 is drawn back through the nasalpharynx, hypopharynx and larynx into the transtracheal opening 60. This screw attachment 64 is then removed and the proximal end of the catheter 60 is sutured in place at the transtracheal opening 62 using a metal locking button 66 as illustrated in FIG. 4D. The length of the catheter tube 11 must be sufficient to allow movement between the locking button 62 and the securement of the arms 21 in the bronchi for normal respiration movement.

When radioactive wires are to be inserted into the catheter 11, the tip of the catheter will be identified and attached to the appropriate connector if a high dose rate afterloader is to be used or a low dose radiation radioactive wire may be inserted to the previously measured depth.

After the scheduled treatment plan has been completed, the catheter is removed. The removal process is that as described in FIG. 3. The locking button 62 is removed and an outer sleeve 29 is moved over the catheter 11. This is then pushed on to the arms 29 at the distal end of the catheter. Once the catheter 11 and the arms 21 have been withdrawn into the outer sleeve 29 the entire system is removed through the transtracheal opening 60. The transtracheal entrance site 60 will heal without the necessity for surgery since it is only a puncture wound of, for example, a 14 gauge needle.

The just described procedure is a closed system that allows radioactive sources to be implanted on a daily basis into the bronchial tree without trauma to the larnyx. Although the system is implanted at the time of the initial fiber optic broncoscopy, it may be utilized for several days after the broncoscopy for delivery of treatment. It should also be noted that by attaching the catheter 11 to a small peripheral bronchiole 47 of the lungs 49, a high degree of safety is provided because peripheral bronchioles are surrounded by alveolar tissue which has only small arteries and veins so the chance of bleeding is greatly reduced.

The transtracheal connection of FIGS. 4 may also be used to provide a sensor to control the delivery of transtracheal oxygen to the lungs during the inspiratory phase of the respiratory cycle.

With the distal end A of the catheter 11 lodged in the peripheral bronchiole 52, the distal end moves about 1 to 2 cm with each movement of the diaphragm during the respiratory cycle with respect to the transtracheal secured proximal end. Thus, during inspiration, the catheter 11 is pulled down as illustrated in FIG. 5B. and during expiration, the catheter 11 moves upwards as illustrated in FIG. 5A.

A flow valve 70 is positioned between the proximal and distal ends of a transtracheal $O_2$ catheter 11 adapted to provide oxygen at the tracheal junction 54. The flow valve 70 is preferably an electronic or a mechanical pulse valve which delivers a predetermined amount of oxygen to the lungs upon actuation. Actuation of the valve 70 is triggered by the downward movement of the distal end of the catheter 11 relative to the flow valve 70 which provides either a mechanical or electrical actuation of the valve 70, depending on the type of valve used.

This arrangement not only controls the valve 70 so that oxygen is delivered only on the inspiratory phase of the respiration cycle, but also results in the movement of the valve 70 away from the tracheal wall during the delivery of oxygen to thereby minimize the accumulation of mucus.

A specific mechanical valve is illustrated in FIGS. 5A and 5B. A valve housing or cap 72 is connected to the distal end of the catheter and includes an oxygen carrying tube 74 extending therein. The oxygen tube 74 includes an opening 76 which, in the position 5A, lies within the housing or cap 72. For downward movement of the catheter 11 during inspiration, the attached housing moves downwardly with respect to tube 74 such that the opening 76 is external of the cap 72 which, in the position 5B, provides oxygen. A spring 78 may be provided between the end of the tube 74 and the housing 72.

FIG. 6 illustrates a double lumen tube 80, 82 used as a transtracheal oxygen catheter. The catheter 11 with the arms 21 may include an electronic sensor 84 sending a signal up wire 86 through the proximal end to an electronic piece of equipment. The sensor 84 senses relative motion. This may be an electronic, electrical or mechanical device, switch or motion sensor. The double lumen tube 80 and 82 may be removed for daily cleaning avoiding mucous plug accumulation. The small transtracheal catheter wire is left in place as a guide for the double lumen catheter 80 and 82 during removal and insertion for daily cleaning. The electrical signal is used to control an electronic valve to produce the oxygen flow during the appropriate portion cycle.

Although the specific securing device having arms 21 as illustrated in FIGS. 5A, 5B and 6, any other form of securing device may be used. The ability to sense the appropriate portion of the respiratory cycle by the motion of the bronchia with respect to other portions of the body is dependent on the securement of the device to the bronchia. Although the specific embodiment of FIGS. 3 using the arms 21 is preferred, any other device which would provide appropriate securement can also be used in this inventive method.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed is:

1. A fixable catheter for use in advancing and withdrawing a radioactive source therethrough to and from a site within a patient's body for treatment of a tumor at said site, comprising:

hollow tube means having an unobstructed interior passageway between a proximal end and a distal end thereof for allowing passage of an elongate wire having a radioactive source adjacent the top thereof through said passageway, deployable anchor means selectively fixable to body tissue for self-securing said hollow tube means at a desired location within the patient's body in the vicinity of the treatment site, the anchor means including means for penetrating the body tissue, and coupling means connecting the anchor means to the hollow tube means at said distal end thereof for precise rigid retention of the distal end of the hollow tube means at said desired location against forces acting in a direction to withdraw the hollow tube means when the anchor means is deployed and fixed to tissue thereat, to permit precise positioning of the radioactive source within the passageway of the hollow tube means relative to the treatment site for irradiation of the tumor when conducting a fractionated therapy regimen over a period of time during which the radioactive source is to be repetitively advanced to and withdrawn from the treatment site.

2. The invention of claim 1, wherein
the coupling means includes means for selectively releasing the anchor means from its fixation to body tissue to permit withdrawl of the hollow tube means, the anchor means and the coupling means from the treatment site.

3. The invention of claim 1, wherein
the coupling means includes means for selectively uncoupling the anchor means from the hollow tube means for removal of the hollow tube means from the patient's body.

4. The invention of claim 3, wherein
the uncoupling means comprises a threaded fastener at the distal end of the hollow tube means for releasing the hollow tube means to permit withdrawal thereof while leaving the anchor means in its deployed tissue engaging position.

5. The invention of claim 1, wherein,
the anchor means includes deployment means for selectively deploying the tissue penetrating means to engage tissue for precise rigid retention of the distal end of the hollow tube means and self-centering thereof in a body duct at the treatment site without obstructing the radioactive source from traversing said passageway to reach the treatment site.

6. The invention of claim 5, wherein
the anchor means includes a storage area for retaining the tissue penetrating means in a non-deployed position during implantation of the catheter in the patient's body.

7. The invention of claim 1, further including
storage means adjacent the tube means for retaining the anchor means in a compressed position until selectively deployed.

8. The invention of claim 7, wherein
the storage means includes second hollow tube means coaxial and substantially coextensive with the first-mentioned hollow tube means and lying outside and spaced from the first-mentioned tube means, the space therebetween forming a retention area for the anchor means.

9. The invention of claim 1, further including:
second hollow tube means coaxial and substantially coextensive with the first-mentioned hollow tube means and slidable over the first-mentioned hollow tube means for selectively forcing disengagement of the anchor means from the tissue when it is desired to withdraw the first-mentioned hollow tube means from the body.

10. The invention of claim 1, wherein
the tissue penetrating means includes at least one spring wire hook held in compression adjacent the tube means during implantation of the catheter in the patient's body.

11. The invention of claim 10, wherein
the spring wire hook comprises stainless steel.

12. The invention of claim 1, wherein
the distal end of the hollow tube means is closed to prevent penetration of tissue and body fluid into the hollow tube means at the treatment site.

13. A device for catheter installation in a patient's body to permit repeated traversal of radioactive source material to and from the site of a malignancy in the patient's body for treatment thereof, said device comprising:
a catheter;
means for implanting the catheter through the site of the malignancy with its distal end extending beyond said site and its proximal end exposed outside the patient's body for access by the radioactive source material, and
anchor means selectively deployable at the distal end of the catheter for penetration of tissue in the immediate vicinity of said distal end beyond said site and self-retention of the distal end of the catheter securely anchored against forces tending to dislodge it, whereby to maintain a substantially constant lineal depth from the proximal end of the catheter to the site of the malignancy so that the radioactive source material may be repeatedly advanced to and withdrawn from said site with assurance of periodic treatments at the precise desired location.

14. The invention of claim 13, further including
disengagement means for releasing the anchor means to free the distal end of the catheter and permit removal of the catheter from the patient's body.

15. The invention of claim 13, wherein
the anchor means includes at least two barbs positioned at opposite sides of the distal end of the catheter for penetration of tissue at opposite sides of a body cavity to substantially center the distal end of the catheter within the body cavity.

* * * * *